(12) United States Patent
Zhao et al.

(10) Patent No.: US 11,660,374 B2
(45) Date of Patent: May 30, 2023

(54) BRAIDED SILK SCAFFOLD WITH ADJUSTABLE MECHANICAL AND DEGRADATION PROPERTIES, AND PREPARATION METHOD AND USE THEREOF

(71) Applicant: ZHEJIANG XINGYUE BIOTECHNOLOGY CO., LTD., Hangzhou (CN)

(72) Inventors: Hongshi Zhao, Hangzhou (CN); Xuexian Kuai, Hangzhou (CN); Longkun Chen, Hangzhou (CN)

(73) Assignee: ZHEJIANG XINGUYE BIOTECHNOLOGY CO., LTD., Hangzhou (CN)

( * ) Notice: Subject to any disclaimer, the term of this patent is extended or adjusted under 35 U.S.C. 154(b) by 0 days.

(21) Appl. No.: 16/767,687

(22) PCT Filed: Sep. 25, 2019

(86) PCT No.: PCT/CN2019/107710
§ 371 (c)(1),
(2) Date: May 28, 2020

(87) PCT Pub. No.: WO2020/134241
PCT Pub. Date: Jul. 2, 2020

(65) Prior Publication Data
US 2021/0361829 A1    Nov. 25, 2021

(30) Foreign Application Priority Data
Dec. 29, 2018 (CN) .......................... 201811637878.0

(51) Int. Cl.
*A61L 27/36* (2006.01)
*D04C 1/02* (2006.01)
*A61L 27/58* (2006.01)
*D04C 1/06* (2006.01)

(52) U.S. Cl.
CPC ....... *A61L 27/3662* (2013.01); *A61L 27/3604* (2013.01); *A61L 27/3687* (2013.01); *A61L 27/3691* (2013.01); *A61L 27/58* (2013.01); *D04C 1/02* (2013.01); *D04C 1/06* (2013.01); *A61L 2430/10* (2013.01); *D10B 2211/04* (2013.01)

(58) Field of Classification Search
CPC .................. A61L 27/3691; A61L 27/3604
See application file for complete search history.

(56) References Cited

FOREIGN PATENT DOCUMENTS

| CN | 102107021 A | 6/2011 |
|---|---|---|
| CN | 102293688 A | 12/2011 |
| CN | 103767806 A | 5/2014 |
| CN | 104606713 A | 5/2015 |
| CN | 104606713 B | * 4/2017 |
| CN | 109758262 A | 5/2019 |
| EP | 2210971 A1 | 7/2010 |

OTHER PUBLICATIONS

Silvia Fare, et al., "In Vitro Study on Silk Fibroin Textile Structure for Anterior Cruciate Ligament Regeneration" in Materials Science and Engerring C 33 (2013) 3601-3608.

* cited by examiner

*Primary Examiner* — Kyle A Purdy
(74) *Attorney, Agent, or Firm* — Nolte Lackenbach Siegel

(57) ABSTRACT

The present invention discloses a braided silk scaffold with adjustable mechanical and degradation properties, and a preparation method and use thereof, belonging to the field of three-dimensional scaffold materials for tendon/ligament repair. The preparation method includes braiding at least one silk strand to form a silk core; placing 1-6 bundles of silk cores in a braiding machine, and braiding at least one layer of silk cladding on the surface of the silk cores to form a silk base frame; removing sericin from the silk base frame; soaking the silk base frame in a collagen solution with a concentration of 3-20 mg/ml, and cross-linking the silk base frame in a vacuum thermal cross-linking machine to obtain the silk scaffold. The braided silk scaffold with adjustable mechanical and degradation properties according to the present invention has good mechanical properties and biocompatibility.

7 Claims, 4 Drawing Sheets

BRAIDED SILK SCAFFOLD WITH ADJUSTABLE MECHANICAL AND DEGRADATION PROPERTIES, AND PREPARATION METHOD AND USE THEREOF

The present application claims priority to the Chinese Patent Application No. 201811637878.0, filed with the China National Intellectual Property Administration (CNIPA) on Dec. 29, 2018, and entitled "BRAIDED SILK SCAFFOLD WITH ADJUSTABLE MECHANICAL AND DEGRADATION PROPERTIES AND PREPARATION METHOD THEREOF", which is incorporated herein by reference in its entirety.

TECHNICAL FIELD

The present invention relates to the field of three-dimensional scaffold materials for tendon/ligament repair, and in particular, to a braided silk scaffold with adjustable mechanical and degradation properties, and a preparation method, and use thereof.

BACKGROUND

With the continuous development of China's economy and the improvement of living standard, Chinese people have obviously shown increasing enthusiasm for participating in physical exercises and competitions. As a result, the incidence of sports injuries has also increased significantly, with tendon/ligament injuries accounting for a half or more of sports injuries. The course of sports system injury, especially tendon/ligament injury, is slow, with poor treatment effects, which not only seriously affects the quality of life of patients, but also brings heavy economic burden to the society.

At present, the repair of ligament and tendon injury mainly depends on direct suture, autograft, allograft, xenograft, and prosthesis materials. However, these surgical or regeneration techniques have their inherent shortcomings, such as recurrent tearing, donor deficiency, donor site complications, immunological rejection, and poor scaffold integration.

In view of the shortcomings of current clinical treatment methods, it is necessary to turn the research on tendon/ligament repair to degradable biomaterials and tissue engineering methods. Silk, as a natural biomaterial approved by FDA, is widely used in the field of tissue engineering due to its excellent mechanical properties, low cost, and good biocompatibility, and many related researches focus on the application of silk scaffold composite with other materials to promote tendon/ligament regeneration. Silk is a natural biomacromolecule material with the strongest biomechanical properties in nature. Its mechanical strength can completely meet the requirements in daily activities of human tendons/ligaments. However, the mechanical properties of this silk scaffold decrease rapidly after implantation in vivo. After in-situ repair in vivo, the silk scaffold soon breaks due to its excessively low mechanical properties, which are lower than the physiological mechanical requirements, leading to the failure of ligament regeneration. Moreover, the speed of mechanical loss is more obvious in intra-articular ligaments (such as anterior cruciate ligament) (the mechanical loss is 75%-85% at 8 weeks). This phenomenon of mechanical loss after implantation greatly limits the clinical application of the braided silk tissue engineering ligament.

At present, in many studies, various types of silk scaffolds have been used for anterior cruciate ligament regeneration, and histology and gene level and the like have proved that silk scaffolds can be used as scaffolds for cell ingrowth and promote cell differentiation towards tendon. However, after implantation in vivo, almost all the existing silk scaffolds have lost their mechanical properties very quickly and have poor mechanical properties, which greatly limits the clinical application and clinical translation of the silk scaffolds. It is still a great challenge how to construct an artificial silk tendon/ligament that can maintain mechanical properties in vivo for a long time and has practical clinical translational prospects.

SUMMARY

In order to overcome the shortcomings of the prior art, the present invention provides a braided silk scaffold with adjustable mechanical and degradation properties, and a preparation method and use thereof. The braided silk scaffold has good mechanical properties and biocompatibility, can maintain the mechanical properties for a long time after in vivo implantation, and can regulate the thickness and the degradation time in vivo by changing the braiding mode of the scaffold. The braided silk scaffold can be applied to tendon or ligament repair.

To achieve the above purpose, the present invention provides the following technical solutions.

The present invention provides a method for preparing a braided silk scaffold with adjustable mechanical and degradation properties, including the following steps: step S1: placing at least one silk strand in a braiding machine to braid to form a silk core, wherein the silk strand is formed by combining a plurality of bundles of silk, with 2-6 pieces of silk in each bundle; step S2: placing 1-6 bundles of silk cores in step S1 in the braiding machine, and braiding at least one layer of silk cladding on the surface of the silk cores to form a silk base frame, wherein the silk cladding is formed by braiding a silk strand obtained by combining 8-16 bundles of silk, with 2-8 pieces of silk in each bundle; step S3: removing sericin from the silk base frame; step S4: soaking the silk base frame with the sericin removed in step S3 in a collagen solution with a concentration of 3-20 mg/ml, ultrasonically dispersing for 20-120 min, so that the collagen solution fully enters pores of the silk base frame, then taking out the silk base frame, storing in a refrigerator at −15° C. to −25° C. for 3-5 h, and storing in a refrigerator at −70° C. to −90° C. for 8-12 h; and step S5: drying the silk base frame in step S4 under vacuum, and cross-linking in a vacuum thermal cross-linking machine to obtain the silk scaffold.

Preferably, before step S3, the preparation method further includes repeating step S2.

Preferably, the silk strand is formed by combining 8-16 bundles of silk, with 2-6 pieces of silk in each bundle.

Preferably, the silk has a density of 40-44 den or 20-22 den.

Preferably, the silk core has a diameter of 0.1-2 mm; and the silk base frame has a diameter of 0.5-3 mm.

Preferably, methods for removing the sericin of the silk base frame in step S3 include removal through boiling with a sodium carbonate solution, removal through boiling with a detergent, removal through boiling with boric acid or removal through direct heating.

Preferably, the removal through boiling with a sodium carbonate solution includes soaking the silk base frame in step 2 in a 0.2 wt % $Na_2CO_3$ aqueous solution, boiling for 60-150 min, stirring the solution in a stirrer at 2000-6000 rpm, replacing water 2-5 times during the process, and drying at 30-80° C.

The present invention further provides a braided silk scaffold with adjustable mechanical and degradation properties obtained by the above preparation method, including at least one bundle of silk cores and at least one layer of silk cladding wrapping the silk cores.

Preferably, the silk core has a diameter of 0.1-2 mm; and the silk scaffold has a diameter of 0.5-3 mm.

The present invention further provides use of the above braided silk scaffold with adjustable mechanical and degradation properties in the preparation of a tendon or ligament repair device.

Compared with the prior art, the present invention has the following beneficial effects.

The silk scaffold with adjustable mechanical and degradation properties according to the present invention is braided by a machine, and the thickness of the single silk scaffold and the degradation time in vivo can be adjusted according to the number of pieces of silk, the number of strands of silk, the number of silk cores formed and the number of silk claddings, which can be suitable for repairing almost all tendons/ligaments of a human body.

The silk scaffold with adjustable mechanical and degradation properties according to the present invention has good biocompatibility and extremely low inflammatory reaction, and regenerated tissues are formed around the scaffold and in internal gaps after in vivo implantation, which can promote local remodeling of the scaffold.

The silk scaffold with adjustable mechanical and degradation properties according to the present invention has a wide adjustment range of mechanical properties, can meet the mechanical requirements of different tendons or ligaments of a human body, has a controllable mechanical loss rate in vivo, can provide mechanics in the early stage, and can be degraded in time in the late stage so as to facilitate tendon/ligament structural remodeling.

The silk scaffold with adjustable mechanical and degradation properties according to the present invention has similar characteristics with an autologous tendon/ligament, can directly apply clinical surgical techniques and instruments during anterior cruciate ligament regeneration, and has better clinical translation prospect.

The silk scaffold with adjustable mechanical and degradation properties according to the present invention can be used as a base frame to provide mechanics, can be coated with collagen on this basis in the later stage, and can be coated with other growth factors, small molecules, special cells and the like to promote local tissue repair.

DETAILED DESCRIPTION

Figure 1:
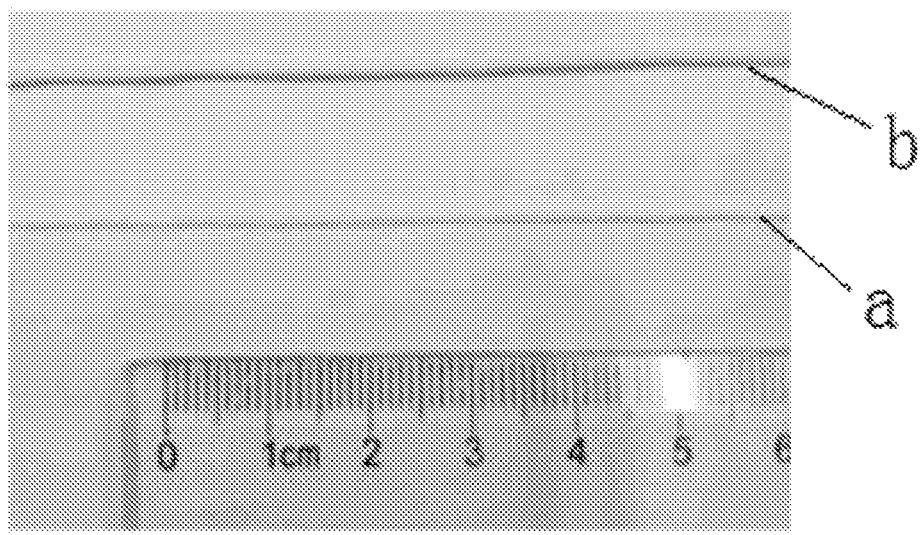
FIG. 1 is an image of a braided silk scaffold.

The present invention is further described below with reference to the accompanying drawings and examples.

The present invention discloses a method for preparing a braided silk scaffold with adjustable mechanical and degradation properties. The preparation method includes the following steps. Step S1: Place at least one silk strand in a braiding machine to braid to form a silk core, where the silk strand is formed by combining a plurality of bundles of silk, with 2-6 pieces of silk in each bundle. Step S2: Place 1-6 bundles of silk cores in step S1 in the braiding machine, and braid at least one layer of silk cladding on the surface of the silk cores to form a silk base frame, where the silk cladding is formed by braiding a silk strand obtained by combining 8-16 bundles of silk, with 2-8 pieces of silk in each bundle. Step S3: Remove sericin from the silk base frame. Step S4: Soak the silk base frame with the sericin removed in step S3 in a collagen solution with a concentration of 3-20 mg/ml, ultrasonically disperse for 20-120 min, so that the collagen solution fully enters pores of the silk base frame, then take out the silk base frame, store in a refrigerator at −15° C. to −25° C. for 3-5 h, and store in a refrigerator at −70° C. to −90° C. for 8-12 h. Step S5: Dry the silk base frame in step S4 under vacuum, and cross-link in a vacuum thermal cross-linking machine to obtain the silk scaffold.

In the present invention, no special requirements are imposed on the kind of silk in each step, and the silk may be various kinds of silk known to those skilled in the art, specifically, such as tussah silk. In the specific example of the present invention, the silk is preferably at a grade 5A or above. In the present invention, the silk preferably has a density of 40-44 den or 20-22 den.

In the present invention, at least one silk strand is placed in a braiding machine to braid to form a silk core.

In the present invention, the silk strand is formed by combining a plurality of bundles of silk, with 2-6 pieces of silk in each bundle, preferably 8-16 bundles of silk, with 2-6 pieces of silk in each bundle. In the present invention, no special requirements are imposed on the model of the braiding machine, and a braiding machine well known to those skilled in the art can be used. In the present invention, the diameter of the silk core is preferably 0.1-2 mm. In the present invention, no special requirements are imposed on the number of the silk strands, and the number can be adjusted according to actual requirements.

In the present invention, after the silk cores are obtained, 1-6 bundles of silk cores are placed in the braiding machine, and at least one layer of silk cladding is braided on the surface of the silk cores to form a silk base frame.

In the present invention, the silk cladding is formed by braiding silk strands obtained by combining 8-16 bundles of silk, with 2-8 pieces of silk in each bundle. In the present invention, the diameter of the silk base frame is preferably 0.5-3 mm. It should be understood that the present invention, this step can be repeated and the number of silk cladding layers is increased to increase the diameter of the silk base frame.

In the present invention, at least one layer of silk cladding refers to that there is one or more layers of silk cladding.

In the present invention, after the silk base frame is obtained, the sericin is removed from the silk base frame.

In the present invention, the methods for removing the sericin from the silk base frame include removal through boiling with a sodium carbonate solution, removal through boiling with a detergent, removal through boiling with boric acid or removal through direct heating.

In the present invention, the removal through boiling with a sodium carbonate solution preferably includes immersing a silk base frame in a 0.2 wt % $Na_2CO_3$ aqueous solution, boiling for 60-150 min, stirring the solution in a stirrer at a rotating speed of 2000-6000 rpm, replacing water 2-5 times during the process, and drying at 30-80° C.

In the present invention, the removal through boiling with a detergent preferably includes soaking the silk base frame in a 0.2 wt % neutral soap solution at a temperature of 95-100° C., at the same time, stirring the solution in a stirrer at a rotating speed of 200-1000 rpm for full degumming, replacing water every 20 min for more than 3 times to ensure that the water temperature is greater than 95° C. during the degumming, and drying at 30-80° C. after degumming.

In the present invention, the removal through boiling with boric acid preferably includes soaking the silk base frame in a 6 wt % boric acid solution at a temperature of 95-100° C., stirring the solution in a stirrer at a rotating speed of 200-1000 rpm for full degumming, replacing water every 20 min for more than 3 times to ensure that the water temperature is greater than 95° C. during degumming, and drying at 30-80° C. after degumming.

In the present invention, the removal through direct heating preferably includes soaking the silk base frame in deionized water, heating to 121° C., degumming at the constant temperature for 30 min, and drying at 30-80° C. after degumming.

In the present invention, the removal of the sericin from the silk base frame can significantly improve the biocompatibility of the silk scaffold and greatly reduce the rejection reaction caused after the silk scaffold is implanted in the human body.

After the removal of the sericin from the silk base frame, in the present invention, the silk base frame is soaked in a collagen solution with a concentration of 3-20 mg/ml and ultrasonically dispersed for 20-120 min, so that the collagen solution fully enters pores of the silk base frame, then the silk base frame is taken out, stored in a refrigerator at −15° C. to −25° C. for 3-5 h, and stored in a refrigerator at −70° C. to −90° C. for 8-12 h to obtain the silk base frame coated with the collagen.

In the present invention, the surface of the silk base frame is coated with the collagen to improve the biocompatibility of the finally obtained silk scaffold, and to promote cell ingrowth and adhesion after the silk scaffold is implanted in vivo.

In the present invention, after being obtained, the silk base frame coated with the collagen is dried under vacuum, and cross-linked in a vacuum thermal cross-linking machine to obtain the silk scaffold.

In the present invention, the vacuum drying is preferably vacuum freeze drying.

In the present invention, the cross-linking is performed for 22-60° C. for one day, then performed at 90-130° C. for two days, and then performed at 55-80° C. for one day. In the present invention, the cross-linking can promote mutual cross-linking of collagen, reduce water solubility of the collagen scaffold and prevent the collagen scaffold from dissolving in vivo.

The present invention further provides a braided silk scaffold with adjustable mechanical and degradation properties obtained by the preparation method according to the forgoing technical solution, including at least one bundle of silk cores and at least one layer of silk cladding wrapping the silk cores.

In the present invention, the diameter of the silk core is preferably 0.1-2 mm, and the diameter of the silk scaffold is preferably 0.5-3 mm.

The thickness of the single silk scaffold and the degradation time in vivo can be adjusted according to the number of pieces of silk, the number of strands of silk, the number of silk cores formed and the number of silk claddings, which can be suitable for repairing almost all tendons/ligaments of a human body.

The silk scaffold with adjustable mechanical and degradation properties according to the present invention is braided by a machine, and the thickness of the single silk scaffold and the degradation time in vivo can be adjusted according to the number of pieces of silk, the number of strands of silk, the number of silk cores formed and the number of silk claddings, which can be suitable for repairing almost all tendons or ligaments of a human body.

The silk scaffold with adjustable mechanical and degradation properties according to the present invention has a wide adjustment range of mechanical properties, and the maximum load of the single silk scaffold braided with different braiding methods is adjustable about between 5 N and 200 N. The silk scaffold can meet the mechanical requirements of different tendons or ligaments of a human body, has a controllable mechanical loss rate in vivo, can provide mechanics in the early stage, and can be degraded in time in the late stage so as to facilitate tendon/ligament structural remodeling.

The silk scaffold with adjustable mechanical and degradation properties according to the present invention has similar characteristics with an autologous tendon/ligament, can directly apply clinical surgical techniques and instruments during anterior cruciate ligament regeneration, and has better clinical translation prospect.

The present invention further provides use of the braided silk scaffold with adjustable mechanical and degradation properties according to the forgoing technical solution in the preparation of a tendon or ligament repair device. In the present invention, the silk scaffold with adjustable mechanical and degradation properties is used for repairing tendons or ligaments as a biological scaffold.

The present invention has no special requirement for the implementation of application, and a manner well known to those skilled in the art can be used.

The silk scaffold with adjustable mechanical and degradation properties according to the present invention has good biocompatibility and extremely low inflammatory reaction, and regenerated tissues are formed around the scaffold and in internal gaps after in vivo implantation. The silk scaffold with adjustable mechanical and degradation properties according to the present invention can be used as a base frame to provide mechanics, can be coated with collagen on this basis in the later stage, and can be coated with other growth factors, small molecules, special cells and the like to promote local tissue repair.

When the silk scaffold is coated with other growth factors, the preparation of the silk scaffold preferably includes the following steps of: dissolving the growth factors in a collagen solution, soaking the silk base frame obtained in step S3 (i.e., the silk base frame after sericin removal) in the collagen solution containing the growth factors, and dispersing by ultrasound for 20-120 min to cause the collagen solution containing the growth factors to fully enter pores of the silk base frame, then taking out the silk base frame, storing the silk base frame in a refrigerator at −15° C. to −25° C. for 3-5 h, storing the silk base frame in a refrigerator at −70° C. to −90° C. for 8-12 h, and obtaining the silk collagen scaffold coated with the growth factors after freeze-drying and thermal cross-linking.

In the present invention, the growth factor preferably includes stromal cell-derived factor-1 (SDF-1 for short) or insulin-like growth factor-1 (IGF-1 for short). When the silk scaffold is coated with the SDF-1, the concentration of the SDF-1 in the collagen solution is preferably 2 ng-1 ug/ml; and when the silk scaffold is coated with the IGF-1, the concentration of the IGF-1 in the collagen solution is preferably 2 ng-1 ug/ml.

When the silk scaffold is coated with special cells, the preparation of the silk scaffold preferably includes the following steps of: fully hydrating the silk scaffold (cross-linked) obtained in step S5, uniformly inoculating special cell suspension on the silk scaffold, maintaining a wet state of the scaffold, placing the silk scaffold in a 37° C. cell incubator for culture for 2 h, and after full cell adhesion, taking out the silk scaffold for later use to obtain the silk scaffold with the surface coated with the special cells.

In the present invention, no special requirements are imposed on the types of the special cells, and the special cells specifically may be tendon stem cells, tendon cells, adipose stem cells, mesenchymal stem cells, etc.

In the present invention, the hydration preferably includes soaking the silk scaffold in 100% alcohol for 30 min and 75% alcohol for 2.5 h in sequence, and then washing away the residual alcohol on the silk scaffold with a PBS solution.

The braided silk scaffold with adjustable mechanical and degradation properties, and the preparation method and use thereof according to the present invention are described in detail with reference to examples below, but they cannot be construed as limiting the claimed scope of the present invention.

EXAMPLE 1

Figure 2:
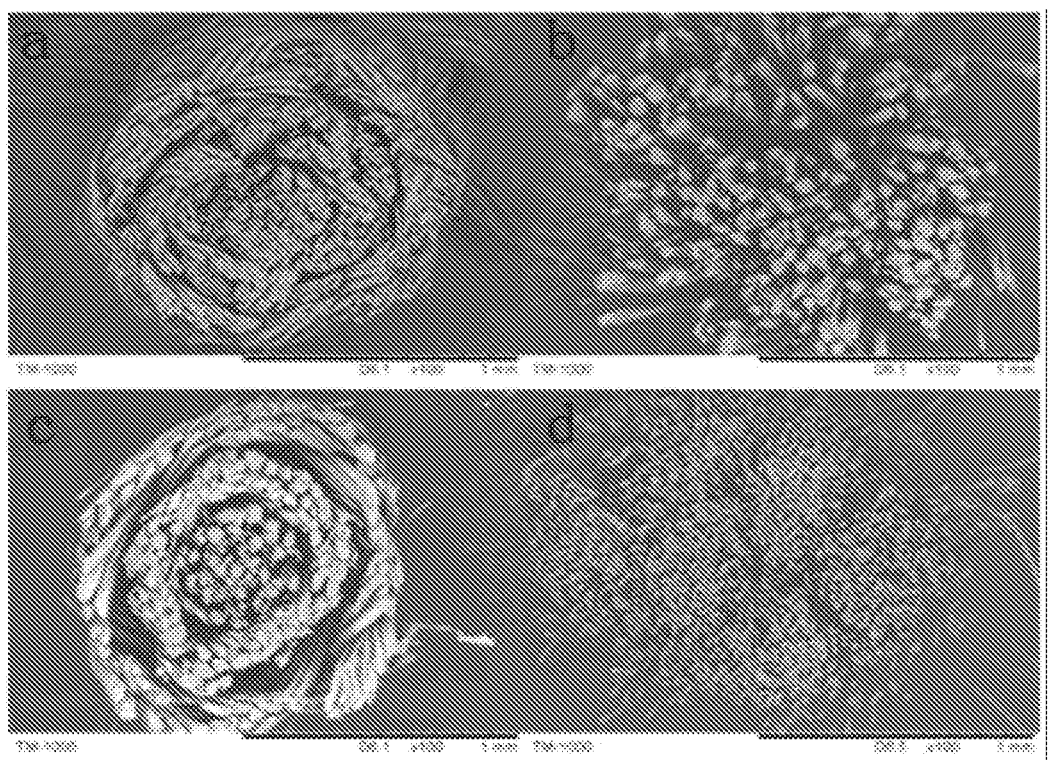
FIG. 2 shows SEM images of surfaces and cross sections of a braided silk scaffold before and after degumming.

Mulberry raw silk was placed on a high-speed rope braiding machine, and 8 bundles of silk with 4 pieces of silk in each bundle were stranded, and a silk core was braided to obtain a silk core a with a diameter of 0.2 mm (a total of 32 silk fibers), referring to FIG. 1. Mulberry raw silk was placed on a high-speed rope braiding machine, and 16 bundles of silk with 5 pieces of silk in each bundle were stranded, and a silk cladding was directly braided on a silk core outer layer to obtain two layers of core cladding in total, so that a braided silk base frame b with a diameter of 1 mm (a total of 192 silk fibers) was obtained, referring to FIG. 1. 6 silk cores were connected in parallel to obtain a first scaffold (8×4×6=192 silk fibers), one silk core was braided with two layers of silk cladding to obtain a second scaffold (16×5+16×5+8×4=192 silk fibers), and the numbers of the silk fibers used were exactly the same. Referring to FIG. 2, the first scaffold (shown in FIG. 2*b*) and the second scaffold (shown in FIG. 2*a*) were observed under a silk scaffold scanning electron microscope. The silk base frame was soaked in 0.2% $Na_2CO_3$ aqueous solution, boiled for 60 min and stirred by a stirrer at 3000 rpm, water was replaced 4 times during the process, the silk base frame was dried at 45° C., and after degumming, the first scaffold (shown in FIG. 2*d*) and the second scaffold (shown in FIG. 2*c*) were observed under the silk scaffold scanning electron microscope.

Figure 3:
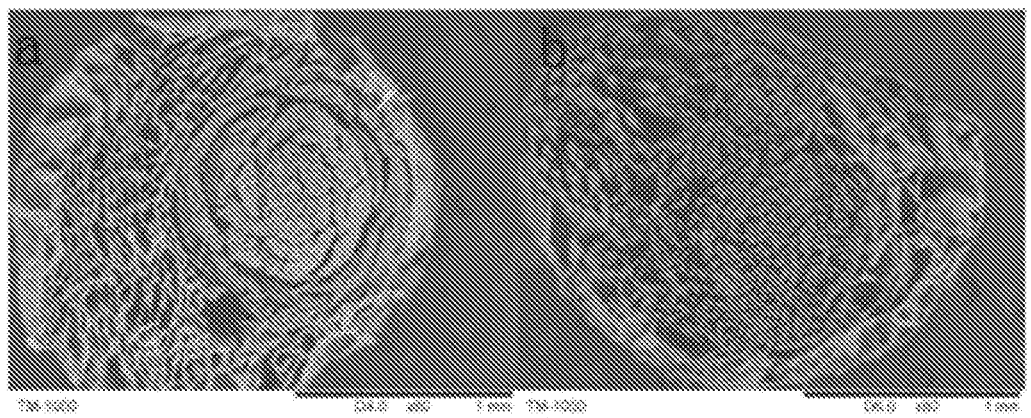
FIG. 3 is an SEM image of a braided silk scaffold combined with collagen.

The first scaffold and the second scaffold were soaked in a collagen solution, ultrasonically treated at 4° C. for 20 min and vacuumized for 2 h; the foregoing steps were repeated 5 times to make the collagen solution fully enter internal gaps of the scaffold, and then the scaffold was taken out, stored in a refrigerator at −20° C. for 4 h, stored in a refrigerator at −80° C. overnight and freeze-dried in a freeze-drying oven for 48 h; the scaffold was cross-linked by a vacuum thermal cross-linking machine at 22° C. for 1 day, at 110° C. for two days and at 65° C. for 1 day, and observed under the silk scaffold scanning electron microscope. Referring to FIG. 3, the state of the first scaffold is shown in FIG. 3*b*, and the state of the second scaffold is shown in FIG. 3*a*.

EXAMPLE 2

Use of a silk scaffold with adjustable mechanical and degradation properties in repair of anterior cruciate ligament injury was tested.

(1) Establishment of an animal model: After 5 female rabbits of about 2500 g were intravenously anaesthetized, their skin and fascia were cut and their joint cavities were opened to remove fat pads therein, anterior cruciate ligaments were fully exposed and completed cut off, and anterior cruciate ligament stumps were removed.

(2) Scaffold implantation: The left and right of the same rabbit were taken as control, and an experimental group used a second scaffold to reconstruct the anterior cruciate ligament, while a control group used a first scaffold to reconstruct the anterior cruciate ligament. Bone tunnels with a diameter of 2 mm were drilled at the femoral and tibial ends respectively by a drill bit with a diameter of 2 mm, the hydrated first scaffold and second scaffold passed through the bone tunnels respectively, and both ends of the scaffold were fixed by interface bone screws with a diameter of 2 mm respectively.

Figure 4:
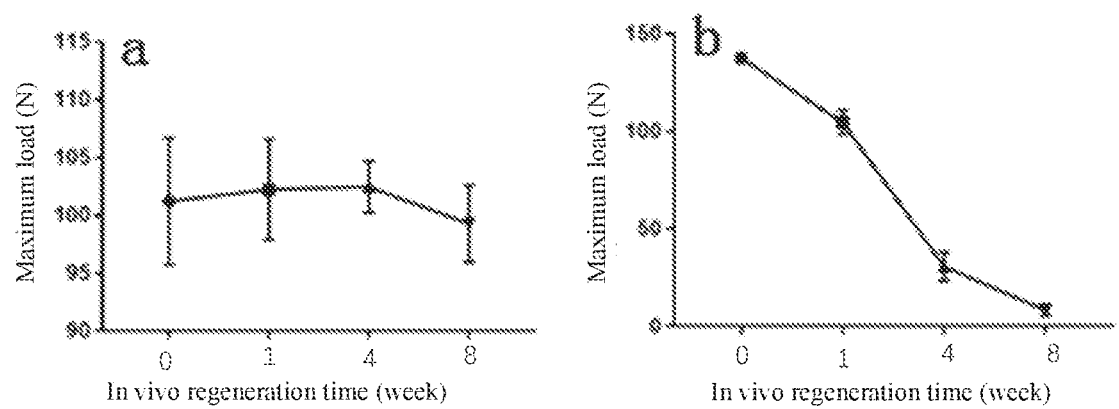
FIG. 4 shows images of maximum load mechanical strengths at different time points after anterior cruciate ligament regeneration.
Figure 5:
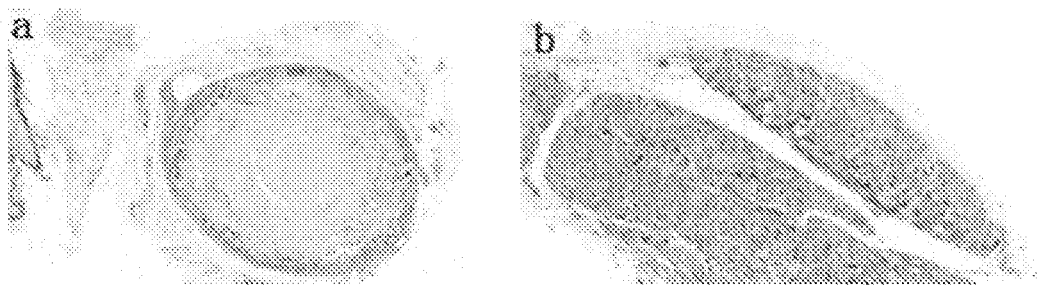
FIG. 5 shows histological images 8 weeks after anterior cruciate ligament regeneration.

(3) Tissue repair capacity: 8 weeks after operation, the rabbit anterior cruciate ligament was taken out and the mechanical level of the anterior cruciate ligament was tested (using a mechanical tester: Instron 5543; and a screw side action tensile fixture). Mechanical test results: Referring to FIG. 4, the mechanics of the experimental group basically did not decrease at 8 weeks (as shown in FIG. 4*a*), while the mechanics of the control group decreased by 80% or more at 8 weeks (as shown in FIG. 4*b*), which indicates that the braiding method of the second scaffold can obviously delay the mechanical decrease. HE staining result display: Referring to FIG. 5, cells grew around the second scaffold (as shown in FIG. 5*a*), and cells grew into the first scaffold (as shown in FIG. 5*b*).

Figure 6:
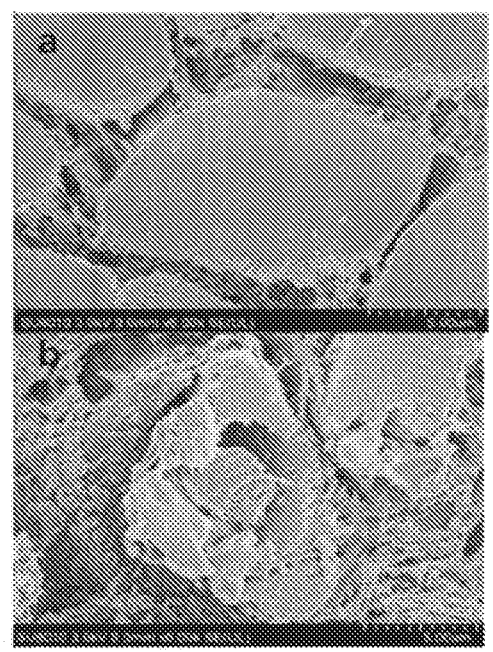
FIG. 6 shows an SEM image of a cross section of a braided silk scaffold 8 weeks after in-situ anterior cruciate ligament regeneration.
Figure 7:
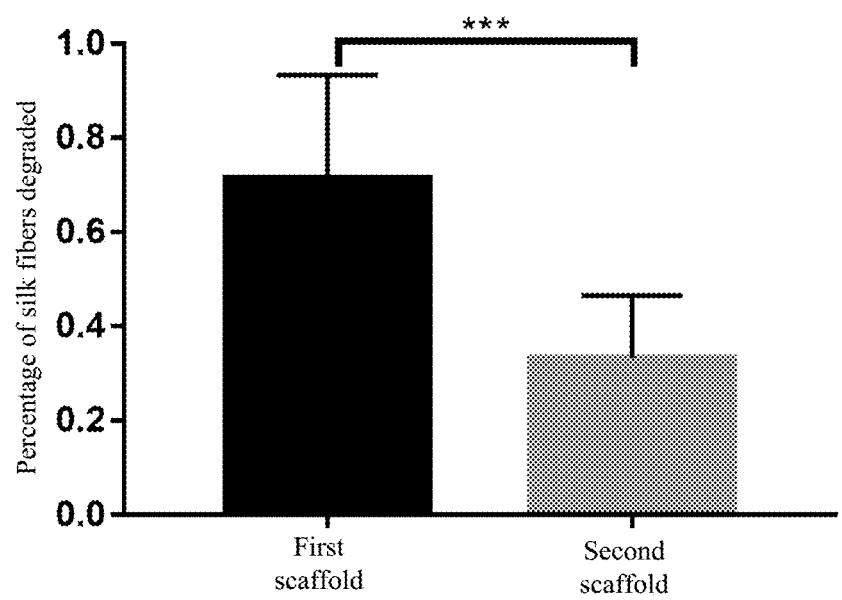
FIG. 7 is a degradation percentage graph of a braided silk scaffold 8 weeks after in-situ anterior cruciate ligament regeneration.

The cross section of the silk scaffold taken out 8 weeks after anterior cruciate ligament regeneration was tested by a scanning electron microscope, and the results are shown in FIG. 6. Although there were some cracks in the cross section of the second scaffold (as shown in FIG. 6*a*) in the experimental group, the cross sections of most silk fibers were kept good, while the first scaffold (as shown in FIG. 6*b*) in the control group had obvious a crack-like structure, which indicates that the degradation proportion of the first scaffold was significantly greater than that of the second scaffold. This further proves that the silk scaffold obtained by the preparation method of the present invention can delay the mechanical loss of the silk scaffold in vivo, and also indicates that the degradation time of the silk scaffold in vivo can be regulated by changing the braiding mode of the scaffold. The specific degradation percentage is shown in FIG. 7. FIG. 7 shows that 8 weeks after the anterior cruciate ligament was reconstructed in situ, the degradation percentage of silk fibers in the first scaffold in the control group was as high as about 72%, while that in the second scaffold in the experimental group was only about 36%.

The above description of the example is only for helping to understand the method of the present invention and its core idea. It should be noted that, several improvements and modifications may be made by persons of ordinary skill in the art without departing from the principle of the present invention, and these improvements and modifications should also be considered within the protection scope of the present invention. Various modifications to these examples are readily apparent to persons skilled in the art, and the generic principles defined herein may be practiced in other examples without departing from the spirit or scope of the present invention. Thus, the present invention is not limited to the examples shown herein but falls within the widest scope consistent with the principles and novel features disclosed herein.

What is claimed is:

1. A method for preparing a braided silk scaffold with adjustable mechanical and degradation properties, comprising the following steps:
    step S1: placing at least one silk strand in a braiding machine to braid to form a silk core, wherein the at least one silk strand is formed by arranging a plurality of bundles of silk in parallel, with 2-6 threads of silk in each bundle;
    step S2: placing 1-6 bundles of silk cores from step S1 into the braiding machine, and braiding at least one layer of silk cladding on a surface of the silk cores to form a silk base frame, wherein the at least one layer of silk cladding is formed by braiding a silk strand obtained by arranging 8-16 bundles of silk in parallel, with 2-8 threads of silk in each bundle;
    step S3: removing sericin from the silk base frame;
    step S4: soaking the silk base frame, after removal of the sericin in step S3, in a collagen solution with a concentration of 3-20 mg/ml, ultrasonically dispersing for 20-120 min, so that the collagen solution fully enters pores of the silk base frame, then taking out the silk base frame, storing the silk base frame in a first refrigerator at −15° C. to −25° C. for 3-5 h, and then storing the silk base frame in a second refrigerator at −70° C. to −90° C. for 8-12 h;
    and step S5: drying the silk base frame in step S4 under vacuum, and cross-linking in a vacuum thermal cross-linking machine to obtain the braided silk scaffold.

2. The preparation method according to claim 1, wherein before step S3, the method further comprises repeating step S2.

3. The preparation method according to claim 1, wherein the at least one silk strand is formed by combining 8-16 bundles of silk, with 2-6 threads of silk in each bundle.

4. The preparation method according to claim 1, wherein silk utilized in the preparation method has a density of 40-44 den or 20-22 den.

5. The preparation method according to claim 1, wherein the silk core has a diameter of 0.1-2 mm; and the silk base frame has a diameter of 0.5-3 mm.

6. The preparation method according to claim 1, wherein removing the sericin of the silk base frame in step S3 comprises at least one of: removal through boiling with a sodium carbonate solution, removal through boiling with a detergent, removal through boiling with boric acid, or removal through direct heating.

7. The preparation method according to claim 6, wherein the removal through boiling with a sodium carbonate solution comprises soaking the silk base frame from step S2 in a 0.2 wt % $Na_2CO_3$ aqueous solution, boiling for 60-150 min, stirring the solution in a stirrer at 2000-6000 rpm, replacing water 2-5 times during the process, and drying at 30-80° C.

* * * * *

UNITED STATES PATENT AND TRADEMARK OFFICE
CERTIFICATE OF CORRECTION

PATENT NO. : 11,660,374 B2  
APPLICATION NO. : 16/767687  
DATED : May 30, 2023  
INVENTOR(S) : Hongshi Zhao, Xuexian Kuai and Longkun Chen Page 1 of 1

It is certified that error appears in the above-identified patent and that said Letters Patent is hereby corrected as shown below:

On the Title Page

Item (73) The assignee information is currently listed as:  
ZHEJIANG XINGUYE BIOTECHNOLOGY CO., LTD.  
Should read:  
ZHEJIANG XINGYUE BIOTECHNOLOGY CO., LTD.

Signed and Sealed this  
Twenty-seventh Day of June, 2023

Katherine Kelly Vidal  
*Director of the United States Patent and Trademark Office*